(12) United States Patent
Brannan

(10) Patent No.: US 9,693,824 B2
(45) Date of Patent: *Jul. 4, 2017

(54) PERIPHERAL SWITCHING DEVICE FOR MICROWAVE ENERGY PLATFORMS

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/055,114

(22) Filed: Feb. 26, 2016

(65) Prior Publication Data

US 2016/0175047 A1 Jun. 23, 2016

Related U.S. Application Data

(63) Continuation of application No. 14/579,560, filed on Dec. 22, 2014, now Pat. No. 9,271,792, which is a (Continued)

(51) Int. Cl.
 *A61B 17/00* (2006.01)
 *A61B 18/18* (2006.01)

(52) U.S. Cl.
 CPC ..... *A61B 18/1815* (2013.01); *A61B 2017/00393* (2013.01); *A61B 2018/1823* (2013.01)

(58) Field of Classification Search
 CPC ...... A61B 18/1815; A61B 2017/00393; A61B 2018/1823
 See application file for complete search history.

(56) References Cited

U.S. PATENT DOCUMENTS

| D223,367 S | 4/1972 | Kountz |
|---|---|---|
| 4,190,053 A | 2/1980 | Sterzer |

(Continued)

FOREIGN PATENT DOCUMENTS

| CN | 1103807 A | 6/1995 |
|---|---|---|
| CN | 1473024 A | 2/2004 |

(Continued)

OTHER PUBLICATIONS

Extended European Search Report corresponding to EP 13 18 6409,6, completed Jul. 8, 2013 and mailed Sep. 18, 2013; (11 pages).

(Continued)

*Primary Examiner* — George Manuel

(57) ABSTRACT

An electrosurgical system includes a power source, a microwave applicator, a switching mechanism, and a controller. The power source is configured to generate microwave energy. The microwave applicator is configured to deliver microwave energy from the power source to tissue. The switching mechanism includes a housing having input and output ports. The input port is connectable to the power source and the output port is connectable to the microwave applicator. The housing is configured to house one or more switches therein. The controller is in operative communication with the switching mechanism to toggle the switch from a first state, wherein microwave energy generated by the power source is directed to the microwave applicator to a second state, wherein microwave energy is directed to a resistive load operably coupled to the switching mechanism.

12 Claims, 3 Drawing Sheets

Related U.S. Application Data continuation of application No. 13/464,021, filed on May 4, 2012, now Pat. No. 8,920,410.

(56) References Cited

U.S. PATENT DOCUMENTS

| | | | |
|---|---|---|---|
| D263,020 S | 2/1982 | Rau, III | |
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 4,741,348 A | 5/1988 | Kikuchi et al. | |
| 5,344,435 A | 9/1994 | Turner et al. | |
| D354,218 S | 1/1995 | Van de Peer | |
| 5,569,245 A | 10/1996 | Guglielmi et al. | |
| 5,718,719 A * | 2/1998 | Clare | A61B 18/12 607/5 |
| 5,830,212 A | 11/1998 | Cartmell et al. | |
| D424,693 S | 5/2000 | Pruter | |
| D424,694 S | 5/2000 | Tetzlaff et al. | |
| D425,201 S | 5/2000 | Tetzlaff et al. | |
| 6,228,079 B1 | 5/2001 | Koenig | |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| 7,553,309 B2 | 6/2009 | Buysse et al. | |
| D606,203 S | 12/2009 | Husheer et al. | |
| D613,412 S | 4/2010 | DeCarlo | |
| D634,010 S | 3/2011 | DeCarlo | |
| 7,993,338 B2 | 8/2011 | Klimovitch et al. | |
| 8,174,267 B2 | 5/2012 | Brannan et al. | |
| D681,810 S | 5/2013 | DeCarlo | |
| 8,920,410 B2 | 12/2014 | Brannan | |
| 9,271,792 B2 | 3/2016 | Brannan | |
| 2008/0319434 A1 | 12/2008 | Rick et al. | |
| 2009/0163907 A1 | 6/2009 | Jarrard et al. | |
| 2010/0082024 A1 | 4/2010 | Brannan et al. | |
| 2010/0082025 A1 | 4/2010 | Brannan et al. | |
| 2010/0286686 A1 | 11/2010 | Hancock | |
| 2012/0239025 A1 | 9/2012 | Smith | |

FOREIGN PATENT DOCUMENTS

| | | |
|---|---|---|
| CN | 1798530 A | 7/2006 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 2045620 A | 11/1980 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 6/2000 |

(56) References Cited

FOREIGN PATENT DOCUMENTS

| WO | 00/36985 A2 | 6/2000 |
|---|---|---|
| WO | 2010/035831 A1 | 4/2010 |

OTHER PUBLICATIONS

European Examination Report, dated Jun. 11, 2015, corresponding to European patent application No. 13166409.6; 4 pages.
Alexander et al., "Magnetic Resonance Image-Directed Stereotactic Neurosurgery: Use of Image Fusion with computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radio!, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizes Use with Rigid-Compression. Mammographic Systems," Radiology 157(2):537-538.

(56) References Cited

OTHER PUBLICATIONS

U.S. Appl. No. 14/011,438, filed Aug. 27, 2013, inventor: Ohri.
U.S. Appl. No. 14/242,019, filed Apr. 1, 2014, inventor: Brannan.
U.S. Appl. No. 14/242,048, filed Apr. 1, 2014, inventor: Prakash.
U.S. Appl. No. 14/281,264, filed May 19, 2014, inventor: Prakash.
U.S. Appl. No. 14/281,344, filed May 19, 2014, inventor: Shiu.
U.S. Appl. No. 14/300,824, filed Jun. 10, 2014, inventor: Behnke.
U.S. Appl. No. 14/300,871, filed Jun. 10, 2014, inventor: Bonn.
U.S. Appl. No. 14/306,865, filed Jun. 17, 2014, inventor: Brannan.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol , vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 110-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 14/011,414, filed Aug. 27, 2013, inventor: Ohri.

(56) References Cited

OTHER PUBLICATIONS

Chinese Office Action and Search Report (with English translation) dated Oct. 17, 2016, corresponding to Chinese Application No. 201310221920.1; 23 total pages.

* cited by examiner

PERIPHERAL SWITCHING DEVICE FOR MICROWAVE ENERGY PLATFORMS

CROSS REFERENCE TO RELATED APPLICATIONS

This application is a continuation application of U.S. patent application Ser. No. 14/579,560, filed on Dec. 22, 2014, which is a continuation application of U.S. patent application Ser. No. 13/464,021, filed on May 4, 2012 (now U.S. Pat. No. 8,920,410), the entire contents of each of which are incorporated by reference herein.

BACKGROUND

Technical Field

The present disclosure relates to peripheral switching devices and more particularly, to an in-line switching mechanism configured to control power output from a microwave generator to a microwave applicator.

Background of Related Art

Electrosurgical systems that utilize microwave generators in conjunction with microwave applicators to treat tissue, e.g., ablate tissue, are well known in the art. Conventional microwave generators are configured to provide microwave energy to the microwave applicator for a specific time frame, e.g., a duty cycle. In certain instances, however, it may prove necessary (or advantageous) to shut the power off prior to the termination of duty cycle. For example, the microwave applicator may need to be moved to a different area on the tissue being treated or to a different location within a patient. Typically, one or more of the "at-the-generator" controls on the microwave generator are activated to terminate or interrupt the duty cycle. In certain instances, for example, to terminate or interrupt the duty cycle, an on/off and/or a reset switch on microwave generator may be pressed. Typically, it is a surgical assistant and not a surgeon that presses these switches. While this approach to control the microwave generator may be effective under some surgical scenarios, hand/foot switching to control the microwave generator may prove advantageous. For example, hand/foot switching capabilities allow a surgeon to directly control the microwave generator, instead having to rely on a surgical assistant.

SUMMARY

In view of the foregoing, an in-line switching mechanism configured to control power output from a microwave generator to a microwave applicator may prove useful in the medical field.

Aspects of the presently disclosed system are described in detail with reference to the drawing figures wherein like reference numerals identify similar or identical elements. As used herein and as is traditional, the term "distal" refers to a portion that is furthest from the user and the term "proximal" refers to a portion of the microwave antenna that is closest to the user. In addition, terms such as "above," "below," "forward," "rearward," etc. refer to the orientation of the figures or the direction of components and are simply used for convenience of description.

An aspect of the present disclosure provides an electrosurgical system that includes a power source, a microwave applicator, a switching mechanism and a controller. The power source is configured to generate microwave energy. The microwave applicator is configured to deliver microwave energy from the power source to tissue. The switching mechanism includes a housing having input and output ports. The input port is connectable to the power source and the output port is connectable to the microwave applicator. The housing is configured to house one or more switches therein. The controller is in operative communication with the switching mechanism to toggle the switch from a first state wherein microwave energy generated by the power source is directed to the microwave applicator to a second state wherein microwave energy is directed to a resistive load operably coupled to the switching mechanism.

The resistive load may be operably disposed within the housing of the switching mechanism and may be in operable communication with the switch.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

In certain instances, the switching mechanism may include one or more microprocessors that communicate with the controller for controlling the switch.

In certain instances, the switching mechanism may further include wireless connectivity electronics such that the controller and microprocessor may communicate with one another wirelessly.

The power source may be a microwave generator and the microwave applicator may be a microwave antenna.

Another aspect of the instant disclosure provides an in-line switching mechanism that is configured to provide communication between a microwave generator and a microwave antenna. The in-line switching element includes a housing that has input and output ports. The input port is connectable to the microwave generator and the output port is connectable to the microwave antenna. The housing is configured to house one or more switches and one or more microprocessors therein. The microprocessor is configured to receive an activation signal from a controller in operable communication with the microwave antenna. Upon receiving the activation signal, the microprocessor toggles the at least one switch from a first state wherein microwave energy produced by the microwave generator is directed to the microwave antenna to a second state wherein microwave energy is directed to a resistive load operably coupled to the in-line switching mechanism.

The resistive load may be operably disposed within the housing of the switching mechanism and may be in operable communication with the switch.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

In certain instances, the switching mechanism may further include wireless connectivity electronics such that the controller and microprocessor may communicate with one another wirelessly.

Yet another aspect of the instant disclosure provides an electrosurgical system that includes a microwave generator, a microwave antenna, a switching mechanism and a controller. The microwave antenna is configured to deliver microwave energy to tissue. The switching mechanism includes a housing having a plurality of ports including a first port connectable to the microwave generator and a second port connectable to the microwave antenna. The housing is configured to house one or more switches, a microprocessor and a power supply therein. The controller is in operative communication with the microprocessor and is configured to provide a command signal to the microprocessor. Upon receiving the command signal, the microprocessor toggles the switch between a first state wherein the switch directs microwave energy to the microwave antenna and a second state wherein the switch directs microwave energy to a resistive load operably coupled to the switching mechanism.

The switch may be a variable attenuator, a one single pole dual throw switch or the like. In certain instances, the variable attenuator may be an absorptive/reflector pin diode attenuator or a digital programmable step attenuator.

The controller may be a finger-switch that is operably disposed on the microwave applicator. Or, in certain instances, the controller may be a footswitch. In this instance, the switching mechanism may further include a third port that is connectable to the footswitch via a cable.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

As noted above, an in-line switching mechanism that is configured to control power output from a microwave generator to a microwave applicator may prove useful in the medical field. To this end, an electrosurgical system utilizing a switching mechanism that is connectable to a power source and a microwave applicator is provided. The switching mechanism includes one or more switches and is in operative communication with a controller to toggle the switch between first and second states. Specifically, in the first state the switch directs microwave energy generated by the power source to the microwave applicator. And, in the second state the switch directs microwave energy to a resistive load operably coupled to the switching mechanism. In accordance with the instant disclosure, a user can directly control microwave energy delivery without having to rely on an assistant to control microwave energy delivery.

Figure 1:
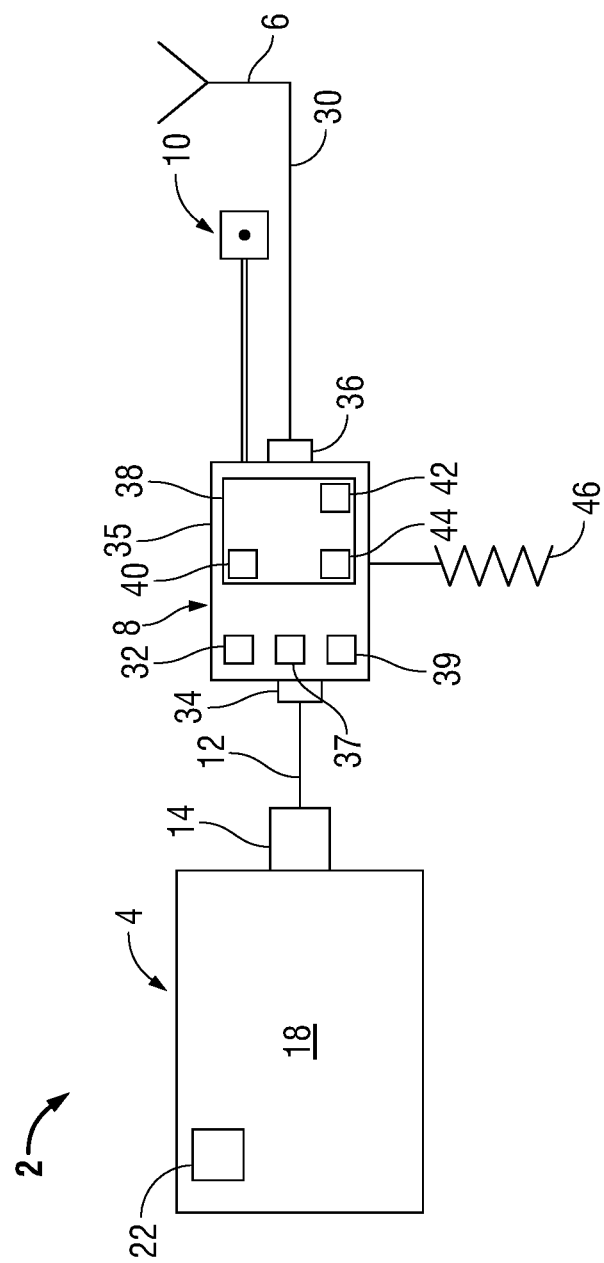
FIG. 1 is a schematic block diagram of a microwave ablation system in accordance with the present disclosure.

FIG. 1 illustrates a schematic block diagram of an electrosurgical system 2 in accordance with an embodiment of the present disclosure. The system 10 includes a power source 4, a microwave applicator 6, a switching mechanism 8 and a controller 10.

Figure 2:
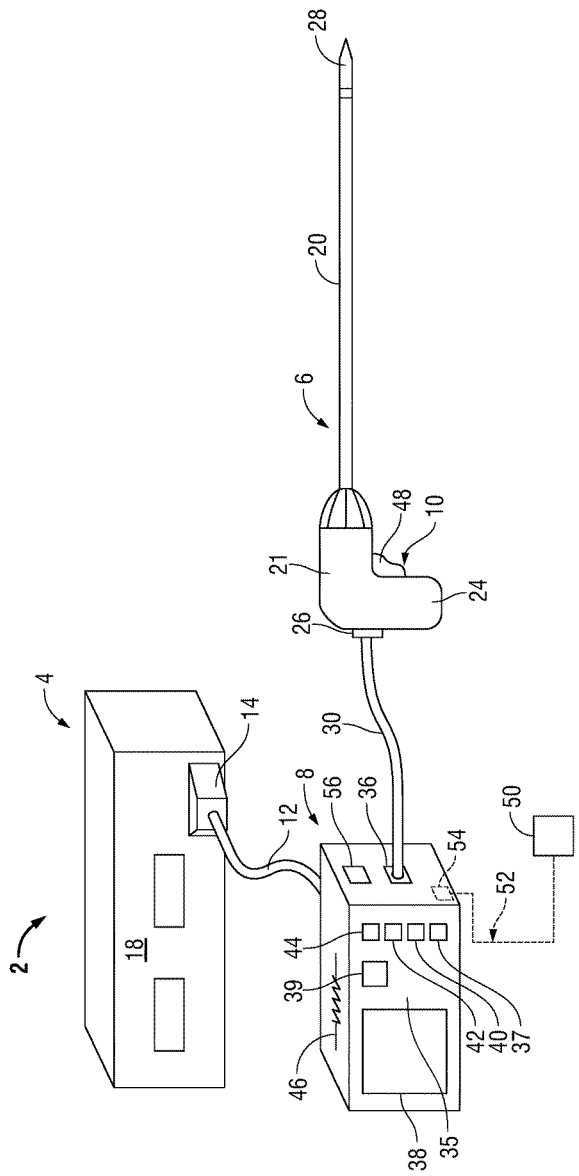
FIG. 2 is a perspective view of the microwave ablation system depicted in FIG. 1.

Power source 4 selectively and removably couples to the switching mechanism 8 via a cable 12 (FIGS. 1 and 2). Cable 12 connects to an output port 14 disposed on the power source 4 and connects to an input port 34 on the switching mechanism 8. Power source 4 is configured to supply electrosurgical energy, e.g., microwave energy, to the microwave applicator 6. In the illustrated embodiment, the power source 4 is a generator 18 and may include a power supply (not explicitly shown) and a microwave output stage (not explicitly shown). In embodiments, generator 18 may also be configured to provide RF energy. The power supply provides DC power to the microwave output stage which then converts the DC power into microwave energy and delivers the microwave energy to the microwave applicator 6 (FIGS. 1 and 2). Generator 18 includes a controller 22 (FIG. 1) that may include analog and/or logic circuitry for processing sensed values provided by one or more modules associated with the generator 18. The controller 22 (or components operably associated therewith) accepts one or more measured signals associated with the microwave applicator 6 when the microwave applicator 6 is radiating energy.

With reference to FIG. 2, microwave applicator 6 includes a housing 21, an elongated shaft 20, a handle 24, and an electrosurgical energy connector 26. Connector 26 is provided at a proximal end of the housing 21 and is configured to connect the microwave applicator 6 to the switching mechanism 8 (FIG. 2). Connector 26 is also configured to supply electrosurgical energy to a conductive tip 28 operably disposed at a distal end of elongated shaft 20 (FIG. 2). In particular, conductive tip 28 and elongated shaft 20 are in electrical communication with connector 26 via an internal coaxial cable (not shown in detail) that extends from a proximal end of the microwave applicator 6 and operatively couples to a radiating section (not shown in detail) operably disposed within the shaft 20 and adjacent the conductive (radiating) tip 28. As is common in the art, the internal coaxial cable may include a dielectric material and an outer conductor that surrounds each of an inner conductor and the dielectric material.

As is conventional in the art, radiating section, by way of conductive tip 28 (or in certain instances without conductive tip 28), is configured to deliver microwave energy to a target tissue site. To this end, elongated conductive tip 28 (and/or shaft 20) may be formed of suitable conductive material including, but not limited to copper, stainless steel or other conductive metals. In certain instances, conductive tip 28 (and/or shaft 20) may be plated with other materials, e.g., gold or silver, to improve certain properties, e.g., to improve conductivity, decrease energy loss, etc. One type of conductive tip that may be utilized with microwave applicator 6 is described in commonly-owned U.S. patent application Ser. No. 12/350,292 filed on Jan. 8, 2009 by Brannan.

Continuing with reference to FIG. 2, housing 21 supports one or more operable components of the microwave applicator 6. In the illustrated embodiment, housing 21 is configured to support the controller 10 (and operable components associated therewith) thereon. In this embodiment, internal circuitry (not shown in detail) associated with the controller 10 is provided in the housing 21 and connects to the switching mechanism 8 via a cable 30 that selectively and releasably couples to connector 26 on the housing 21. One or more leads (not shown) connected to the controller 10 are bundled together with leads of the cable 30 that are configured to provide microwave energy to the radiating section of the microwave applicator 6. The leads of the controller 10 connect to internal circuitry 32 of the switching mechanism 8.

Switching mechanism 8 functions as an in-line switching mechanism and includes a housing 35 that is made from one or more suitable materials, e.g., plastic, metal, ceramic, etc. (FIGS. 1 and 2). Housing 35 includes input and output ports 34 and 36, respectively (see FIGS. 1 and 2). Input port 34 is connectable to input port 14 of the generator 18 via cable 12 and output port 36 is connectable to the microwave applicator 6 via cable 30 that couples to the connector 26 (FIG. 2).

In the illustrated embodiment, housing 35 includes a power supply 37 that is configured to provide power to the internal circuitry of the switching mechanism 8 (FIGS. 1 and 2). Alternately, internal circuitry of the switching mechanism 8 may be energized by the generator 18 (or in certain instances, by the microwave applicator 6).

In embodiments, the housing 35 may be configured to house one or more microprocessors 39 that communicate with the controller 10. Housing 35 may also be configured to house wireless connectivity electronics 56 configured to provide a wireless connection between the controller 10 and microprocessor 39 (and/or the microprocessor 39 and the generator 18) to control one or more functions of the switching mechanism 8, generator 18, and/or microwave applicator 6, as described in greater detail below.

Figure 3A:
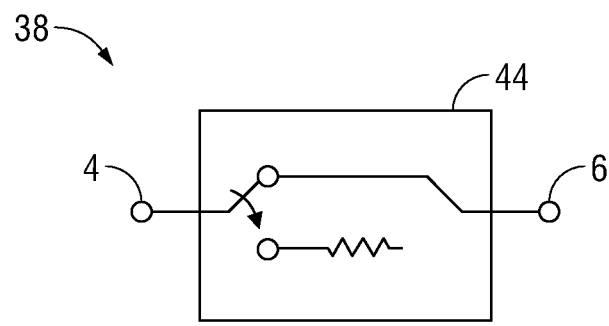
FIGS. 3A-3B are a schematic block diagrams illustrating two types of switching mechanisms that may be utilized with the microwave ablation system depicted in FIGS. 1-2.
Figure 3B:
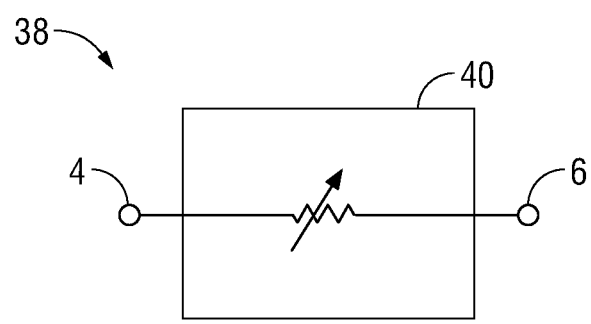

Housing 35 is configured to house one or more switches 38 therein (FIGS. 1 and 2). Switches 38 may be any suitable type of switch. For example, and in the illustrated embodiments, switches 38 can be an electronically variable attenuator. Suitable electronically variable attenuators include, but are not limited to digital programmable step attenuators 40, absorptive/reflective pin diode attenuators 42, and the like (see FIGS. 1-3). Alternately, switch 38 may be a single pole dual throw switch 44 (FIGS. 1 and 2). Regardless of the configuration of switch 38, switch 38 operably couples to a resistive load 46 (FIGS. 1-3).

In the illustrated embodiment, resistive load 46 is provided within the housing 35 and is configured to serve as a "dummy" load. In particular, resistive load 46 is configured to absorb microwave energy that is directed thereto by the switch 38 as a result of the controller 10 providing a control signal to the switch 38.

Controller 10 is in operative communication with the switching mechanism 8 and is configured to toggle the switch 38 from a first state, wherein the switch 38 directs microwave energy from the generator 18 to the microwave applicator 6 to a second state, wherein the switch 38 directs microwave energy to the resistive load 46. To this end, controller 10 may be a finger-switch 48 (FIG. 2) on the microwave applicator 6 (as in the illustrated embodiment) or a footswitch 50 (shown in phantom in FIG. 2). In either instance, the controller 10 communicates a command signal to one of the aforementioned switches 38, e.g., digital programmable step attenuator 40, to toggle the switch 38 between the first and second states.

As illustrated in FIG. 2, finger-switch 48 is supported on the housing 21 of the microwave applicator 6. Finger-switch 48 is depressible by an end user such that upon actuation thereof a command signal is transmitted to one of the aforementioned switches 38 to toggle the switches 38 between the first and second states.

In an embodiment, the footswitch 50 may be configured to function similar to that of the finger-switch 48 and may be utilized to toggle the switch 38 between the first and second states. Unlike the finger-switch 48, however, the footswitch 50 is configured to communicate with the switching mechanism 8 via a cable 52 that is connectable to an optional third port 54 that may be disposed on the housing 35.

While switching mechanism 38 has been described herein as being part of the system 2, it is within the purview of the instant disclosure that the switching mechanism 38 may be configured as a "universal" switching mechanism configured for use with a wide variety of other generators and/or microwave applicators. The specific configuration of controllers 10, however, will depend on the specific configuration of microwave applicator, e.g., a microwave applicator 6 that includes a finger-switch 48 or a microwave applicator that includes a footswitch. In certain embodiments, the footswitch 50 and finger-switch 48 may be utilized in combination with one another.

In use, switching mechanism 38 is coupled to the generator 18 and the microwave applicator 6. For illustrative purposes, it is assumed that the microwave applicator 6 is equipped with a finger-switch 48. Generator 18 is turned on and microwave energy is transmitted to the microwave applicator 6.

In the instance where a surgeon wants to stop transmitting microwave energy to the microwave applicator 6, the surgeon depresses finger-switch 48, which, in turn, transmits a first command signal to one of the aforementioned switches 38. As a result of receiving the command signal, the switch 38 directs microwave energy to the resistive load 46.

Subsequently, the surgeon may depress the finger-switch 48 again, which, in turn transmits a second command signal to the switch 38. As a result of receiving the second command signal, the switch 38 directs microwave energy back to the microwave applicator 6.

System 2 including the switching mechanism 8 overcomes the aforementioned drawbacks associated with conventional electrosurgical systems that utilize microwave generators with at-the-generator controls. In particular, system 2 allows a surgeon to directly control the microwave output to the microwave applicator 6 without the help of a surgical assistant.

From the foregoing and with reference to the various figure drawings, those skilled in the art will appreciate that certain modifications can also be made to the present disclosure without departing from the scope of the same. For example, and as noted above, the housing 35 of the switching mechanism 38 may be configured to house wireless connectivity electronics 56 (FIG. 2). In this instance, the wireless connectivity electronics 56 and microprocessor 39 may be configured provide wireless communication between a surgeon and the switching mechanism 8. Moreover, a transceiver may provide communication between the surgeon and the switching mechanism 8 and may be in the form of a clip (or other suitable device) that attaches to the microwave applicator 6 (or other suitable device or apparel). Alternately, the transceiver may fit in the surgeon's hand, sit on the floor, etc.

In operation, the surgeon simply speaks in a vicinity of the transceiver to toggle the switching mechanism between the first and second states to control microwave energy output to the microwave applicator 6.

In certain instances, the controller 10 may be configured to control other output characteristics of the generator 18, e.g., duty cycle, intensity, etc.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   a power source configured to generate electrosurgical energy;
   an energy applicator configured to deliver electrosurgical energy from the power source to tissue; and
   a switching mechanism including:
      a resistive load; and
      a single pole dual throw switch configured to electrically couple the power source to one of the energy applicator or the resistive load.

2. The electrosurgical system according to claim 1, further comprising a controller configured to toggle the single pole dual throw switch between a first state, wherein the single pole dual throw switch directs energy generated by the power source to the energy applicator, and a second state, wherein the single pole dual throw switch directs energy to the resistive load.

3. The electrosurgical system according to claim 2, wherein the controller is a finger-switch disposed on the energy applicator and electrically coupled to the single pole dual throw switch.

4. The electrosurgical system according to claim 3, wherein the finger-switch is detachably coupled to the energy applicator.

5. The electrosurgical system according to claim 2, wherein the controller is a footswitch electrically coupled to the single pole dual throw switch.

6. The electrosurgical system according to claim 2, wherein the switching mechanism is configured to communicate wirelessly with the controller.

7. The electrosurgical system according to claim 1, wherein the switching mechanism includes:
   a housing having the single pole dual throw switch and the resistive load disposed therein;
   an input port supported on the housing and configured to be coupled to the power source; and
   an output port supported on the housing and configured to be coupled to the energy applicator.

8. The electrosurgical system according to claim 1, further comprising a housing having the single pole dual throw switch disposed therein, wherein the resistive load is remote from the housing.

9. A method of operating an electrosurgical system, comprising:
   toggling a single pole dual throw switch of a switching mechanism between:
      a first state, wherein an electrical connection is formed between a power source and an energy applicator for treating tissue; and
      a second state, wherein the electrical connection between the power source and the energy applicator is opened to electrically connect the power source to a resistive load of the switching mechanism.

10. The method according to claim 9, wherein toggling the single pole dual throw switch between the first state and the second state includes actuating a finger-switch that is wirelessly connected to the single pole dual throw switch.

11. The method according to claim 10, wherein the finger-switch is detachably coupled to the energy applicator.

12. The method according to claim 9, wherein toggling the single pole dual throw switch between the first state and the second state includes actuating a footswitch that is wirelessly connected to the single pole dual throw switch.

* * * * *